(12) United States Patent
Redmond (10) Patent No.: US 10,203,285 B2
(45) Date of Patent: Feb. 12, 2019

(54) APPARATUS, METHODS, AND SYSTEMS FOR HIGH-POWER AND NARROW-LINEWIDTH LASERS

(71) Applicant: Massachusetts Institute of Technology, Cambridge, MA (US)

(72) Inventor: Shawn Redmond, Concord, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 248 days.

(21) Appl. No.: 15/375,910

(22) Filed: Dec. 12, 2016

(65) Prior Publication Data
US 2018/0266959 A1    Sep. 20, 2018

(51) Int. Cl.
| | |
|---|---|
| G01N 21/65 | (2006.01) |
| H01S 3/067 | (2006.01) |
| H01S 3/16 | (2006.01) |
| H01S 3/30 | (2006.01) |
| H01S 3/08 | (2006.01) |
| H01S 3/23 | (2006.01) |

(Continued)

(52) U.S. Cl.
CPC ............. *G01N 21/65* (2013.01); *H01L 33/02* (2013.01); *H01S 3/06791* (2013.01); *H01S 3/08013* (2013.01); *H01S 3/1306* (2013.01); *H01S 3/1628* (2013.01); *H01S 3/2316* (2013.01); *H01S 3/30* (2013.01); *G01N 2201/06113* (2013.01)

(58) Field of Classification Search
CPC .......... G01N 21/65; G01N 21/64; H01S 3/06; H01S 3/08; H01S 3/16; H01S 3/13; H01S 3/30; H01S 3/23
See application file for complete search history.

(56) References Cited

U.S. PATENT DOCUMENTS

| | | |
|---|---|---|
| 5,432,610 A | 7/1995 | King et al. |
| 5,538,850 A | 7/1996 | King et al. |

(Continued)

FOREIGN PATENT DOCUMENTS

WO    WO 2014/021781 A1    2/2014

OTHER PUBLICATIONS

Dahmani, B. et al., "Frequency stabilization of semiconductor lasers by resonant optical feedback," *Optics Letters* (Nov. 1987), vol. 12, pp. 876-878.

(Continued)

*Primary Examiner* — Abdullahi Nur
(74) *Attorney, Agent, or Firm* — Smith Baluch LLP (57) ABSTRACT

A system includes a build-up cavity to locally increase the power of light beams within the build-up cavity, where the light beams interact with samples to sense a substance of interest. The build-up cavity is disposed within a main cavity that includes a gain material to amplify the light beams. A portion of the light beams oscillating in the build-up cavity propagators through the build-up cavity and functions as a feedback to control the linewidth of the light beams. The two cavities can function as two separate "filters" and light beams at wavelengths that propagate through both of these "filters" can be preferentially amplified. The combination of the build-up cavity and the main cavity can achieve high power and narrow linewidth for the light beams without complex electronics, thereby decreasing the size, weight, and power (SWaP) of the system.

21 Claims, 5 Drawing Sheets

(51) Int. Cl.
  H01S 3/13    (2006.01)
  H01L 33/02   (2010.01)

(56) References Cited

U.S. PATENT DOCUMENTS

| | | | |
|---|---|---|---|
| 5,642,375 | A | 6/1997 | King et al. |
| 5,835,522 | A * | 11/1998 | King ................ H01S 3/082 372/97 |
| 6,532,072 | B1 | 3/2003 | Largent |
| 8,315,281 | B2 | 11/2012 | Lin et al. |
| 8,976,834 | B2 | 3/2015 | Kaster et al. |
| 9,019,998 | B1 | 4/2015 | Qureshi |
| 9,110,006 | B1 | 8/2015 | Hovde et al. |
| 2002/0105998 | A1 | 8/2002 | Ksendzov |
| 2007/0237460 | A1 | 10/2007 | Fan et al. |
| 2011/0080579 | A1 | 4/2011 | Pipino |
| 2012/0224167 | A1 | 9/2012 | Sanders et al. |
| 2015/0276481 | A1 | 10/2015 | Liu et al. |

OTHER PUBLICATIONS

International Search Report and Written Opinion dated Sep. 6, 2017 for International Application No. PCT/US2016/68076, 17 pages.

Waechter, H. et al., "Chemical Sensing Using Fiber Cavity Ring-Down Spectroscopy," *Sensors* (2010), 10, pp. 1716-1742.

Zhao, Y. et al., "High-power figure-of-eight fiber laser with passive sub-ring loops for repetition rate control," *Optics Express* (2006), vol. 14, No. 22, pp. 10475-10480.

Breuer, et al., "Investigations of Repetition Rate Stability of a Mode-Locket Quanum Dot Semiconductor Laser in an Auxiliary Optical Fiber Cavity", *IEEE Journal of Quantum Electronics*, Feb. 2010, vol. 46, No. 2, pp. 150-157.

Feng, et al., "Noise suppression, linewidth narrowing of a master oscillator power amplifier at 1.56µm and the second harmonic generation output at 780nm" *Optics Express*, Aug. 4, 2008, vol. 16, No. 16, 7 pages.

Frosch, et al., "Investigation of Gas Exchange Processes in Peat Bog Ecosystems by Means of Innovative Raman Gas Spectroscopy", Anal. Chem, 2013, vol. 85, pp. 1295-1299.

Hippler, "Cavity-Enhanced Raman Spectroscopy of Natural Gas with Optica Feedback cw-Diode Lasers", *Anal. Chem.* Jul. 10, 2015, vol. 87, pp. 7803-7809.

Kachanov, et al., "Cavity-enhanced optical feedback-assisted photoacoustic spectroscopy with a 10.4 µm external cavity auantum cascade laser", *Appl. Phys. B*, Sep. 13, 2013, vol. 110, pp. 47-56.

Lee, et al., "Linewidth reduction of distributed-feedback diode laser using an all-fiber interferometer with short path imbalance" *Review of Scientific Instruments*, Jul. 2011, vol. 82, 19 pages.

Lin, et al. "Long-external-cavity Distributed Bragg Reflector Laser with Subkilohertz Intrinsic Linewidth." *Optics Letters*, Jun. 1, 2012, vol. 37, No. 11, pp. 1989-1991.

Lopez-Mercado, et al., "Locking of the DFB laser through fiber optic resonator on different coupling regimes", *Optics Communications*, Jan. 2016, vol. 359, pp. 195-199.

Manfred, et al., "Optical-feedback cavity-enhanced absorption spectroscopy in a linear cavity: model and experiments", *Appl. Phys. B*, Jul. 2015, vol. 120, Issue 2, pp. 329-339.

Maisons, et al., "Optical-Feedback Cavity-Enhanced Absorption Spectroscopy with a Quantum Cascade Laser", *Optics Letters, Optical Society of America*, Feb. 2010, vol. 35, Issue 21, pp. 3607-3609.

Sato, et al., "Simple Real Time Trace Nitrogen Dioxide Detector Based on Continuous-Wave Cavity Ringdown Spectroscopy Using Passively Locked External Cavity Diode Laser" *Jap. J. Appl. Physics.*, Apr. 6, 2008, vol. 47, pp. 6478-6483.

Ye, et al., "Frequency-Shifted Interferometry—A Versatile Fiber-Optic Sensing Technique", *Sensors*, Jun. 20, 2014, vol. 14, pp. 10977-11000.

* cited by examiner

APPARATUS, METHODS, AND SYSTEMS FOR HIGH-POWER AND NARROW-LINEWIDTH LASERS

GOVERNMENT SUPPORT

This invention was made with Government support under Contract No. FA8721-05-C-0002 awarded by U.S. Air Force. The Government has certain rights in the invention.

BACKGROUND

High-power and narrow-linewidth laser sources can benefit a wide range of applications. For example, high-power and narrow-linewidth lasers operating at about 1.5 µm to about 1.6 µm and second harmonic generation (SHG) at around 780 nm can be useful in quantum optics experiments, such as pumping an optical parametric oscillator (OPO) to generate a non-classical state at telecommunication wavelengths. In another example, 780 nm is the transition wavelength of the D2 line of Rubidium (Rb) atoms, and lasers at this wavelength can be used in atomic physics, such as laser cooling and internal state preparation of Rb atoms. In yet another example, high-power and narrow-linewidth lasers can be used in chemical sensing, such as Raman spectroscopy, to detect trace amounts of toxic substances or explosives.

A conventional technique to control the linewidth of lasers uses an active feedback system to monitor the output beams of the lasers and control the operation of the lasers to achieve the desired linewidth. Active feedback systems typically include complex electronics and detectors, which can be expensive. In applications for chemical sensing, the active feedback system can also increase the size, weight, and power (SWaP) of the resulting sensor, thereby limiting the portability and compactness of the sensor.

SUMMARY

Apparatus, systems, and methods described herein are generally related to high-power and narrow-linewidth lasers for substance sensing. In one example, an apparatus for chemical sensing includes a first resonator and a gain material, disposed within the first resonator, to amplify a laser beam oscillating within the first resonator. The apparatus also includes a second resonator, disposed within the first resonator and in optical communication with the gain material, to receive a sample. A detector is in optical communication with the sample to detect light scattered by interaction between the sample and the laser beam.

In another example, a method of chemical sensing includes amplifying a laser beam with a gain material disposed in a first resonator and coupling the laser beam into a second resonator disposed within the first resonator. The method also includes illuminating a sample disposed within the second resonator, detecting light scattered by the sample, and determining a presence or absence of at least one chemical in the sample based at least in part on the light scattered by the sample.

In yet another example, a system for Raman sensing includes a ring resonator and a gain material, disposed within the ring resonator, to amplify a laser beam propagating within the ring resonator. A linear resonant cavity is disposed within the ring resonator and in optical communication with the gain material to hold a sample that scatters a first portion of the laser beam and to transmit a second portion of the laser beam. The second portion of the laser beam provides passive feedback to determine the frequency of the laser beam. A detector is in optical communication with the sample to detect the first portion of the laser beam.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Overview

To address the need for a high-power narrow-linewidth lasers in applications such as Raman spectroscopy, apparatus, systems, and methods described herein employ an approach using a build-up cavity (also referred to as a build-up resonator or a resonant cavity-enhanced sample cell) to locally increase the power of light beam within the build-up cavity, where the light beam can interact with samples. The build-up cavity is disposed within a main cavity (also referred to as a laser cavity or laser resonator) including a gain material to amplify the light beam. A portion of the light beam oscillating in the build-up cavity transmits through the build-up cavity and functions as a feedback to control the linewidth of the light beam. In other words, the feedback can act to couple together the build-cavity and the main cavity. The two cavities can function like two separate "filters" whose passbands get multiplied together. Light beam at wavelengths that are transmitted by both of these "filters" can be preferentially amplified. In this manner, the combination of the build-up cavity and the main cavity can select the operating wavelength of the resulting system.

Systems using this approach can achieve high power and narrow linewidth without complex and expensive electronics as normally used in active feedback systems. The approach can be conveniently implemented in Raman spectroscopy. As understood in the art, Raman spectroscopy can be a valuable technique for chemical and molecule identification, regardless of whether the chemical or molecule is in gas, liquid, or solid state. Due to the low signal levels, a high-power and narrow-linewidth laser can generate stronger signals for available sensors. The approach described herein can achieve high sensitivities using a smaller laser operating with orders of magnitude less power compared to conventional Raman spectroscopy.

Systems, apparatus, and methods described herein can be further employed in other applications, including but not limited to: chemical identification of gases and airborne particulates, such as pollutant monitoring, emissions testing and monitoring; FDA monitoring of agricultural pesticides; police and department of defense sensors for detection of chemical warfare agents, toxic chemicals, and explosives.

Systems for Chemical Sensing with Build-Up Cavities

Figure 1:
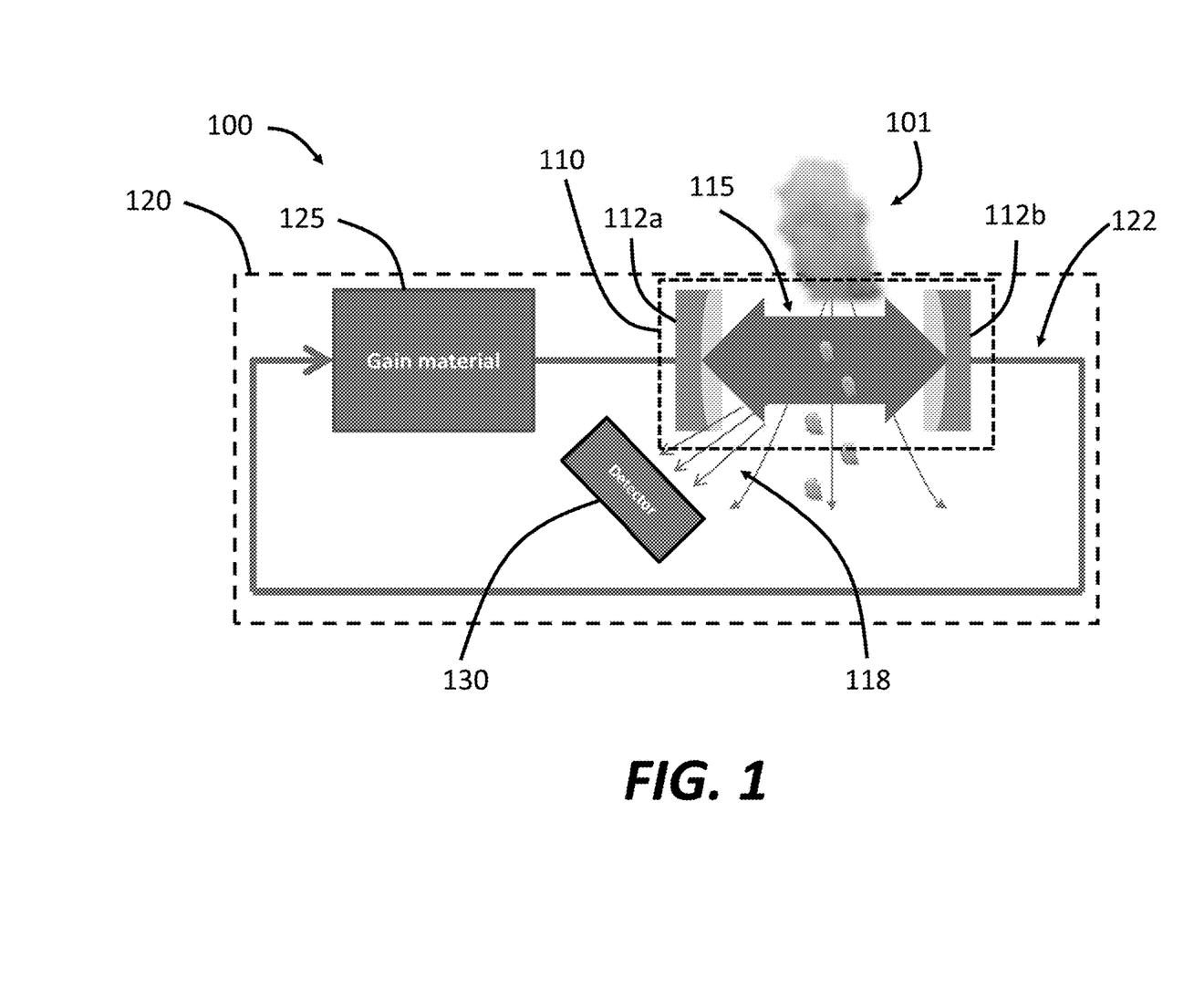
FIG. 1 shows a schematic of a chemical sensing system with a build-up cavity.

FIG. 1 shows a schematic of a system 100 with a build-up cavity 110 disposed within a main cavity 120 for substance sensing. The build-up cavity 110 includes a first reflector 112a and a second reflector 112b disposed opposite the first reflector 112a. A space between the two reflectors 112a and 112b receives a sample 101, which may include substance of interest, such as toxic materials or explosives. The build-up cavity 110 guides a light beam 115, which interacts with the sample 101 to generate scattered light 118. A detector 130 receives the scattered light 118 and generates a detection signal that indicates the presence or absence of the substance of interest.

Part of the light beam 115 passes through the build-up cavity 110 (designated as transmitted beam 122) and propagates into a gain material 125 (also referred to as a gain medium) which amplifies the transmitted beam 122. The amplified transmitted beam 122 then propagates back to the build-up cavity 110 via the main cavity 120. Therefore, the build-up cavity 110 and the gain material 125 are optically coupled together by the light beam 115 and 122 and form a main laser resonator 120 to amplify the transmitted beam 122. The build-up cavity 110, in contrast, does not include a gain material, but the light beam 115 can oscillate between the reflectors 112a and 112b, increasing the strength of light field within the build-up cavity 110, thereby increasing the interaction between the light beam 115 and the sample 101.

The main cavity 120 is configured as a ring resonator utilizing the transmission of the build-up cavity 110 as the optical feedback filter for the gain material 125. This passive feedback can ensure constant operation on resonance inside of the build-up cavity 110 without complex electronics to maintain locking. The optical feedback path (i.e., beam path of the transmitted beam 122) completes the main cavity 120 and controls the spectral linewidth. In one example, the beam path of the transmitted beam 122 can include waveguide components, such as optical fiber, to simplify alignment and mode-matching between components. In another example, the transmitted beam 122 can be reflected by one or more mirrors to form the main cavity 120.

By implementing a ring laser configuration, the system 100 can achieve high power and narrow linewidth for the light beam 115 by utilizing the transmission of the build-up cavity 110 as a feedback mechanism. The system 100 can also decouple the laser spectral width from the build-up cavity 110 through the use of a longer fiber feedback path to propagate the transmitted beam 122. Both aspects can result in significantly narrower spectral operation, thereby improving performance for substance sensing techniques, such as Raman systems, within a much smaller size.

The main cavity 120 can use various types of configurations to amplify the transmitted beam 122. In one example, the main cavity 120 can include a fiber ring resonator, in which case the transmitted beam 122 propagates in a fiber. The gain material 125 may also be disposed in the fiber. For example, the gain material 125 can be a fiber doped with rare earth ions, such as erbium ($Er^{3+}$), neodymium ($Nd^{3+}$), ytterbium ($Yb^{3+}$), thulium ($Tm^{3+}$), or praseodymium ($Pr^{3+}$). The gain material 125, in one example, includes gallium-aluminum-arsenide (GaAlAs). In another example, the gain material 125 can include indium gallium nitride (InGaN). In another example, the main cavity 120 can include a hybrid standing-wave and ring resonator, which typically uses reflectors to construct a cavity, in which the gain material 125 is disposed to amplify the transmitted beam 122. More information about hybrid standing-wave and ring resonator can be seen in U.S. Pat. No. 7,463,666 B2 and U.S. Pat. No. 7,756,186 B2, each of which is hereby incorporated by reference in its entirety.

The gain material 125 can include various types of lasing medium to amplify the transmitted beam 122. The gain material 125 can also generate the beams 115 and 122, in which case the main cavity 120 can function as a laser oscillator. In general, it can desirable for the gain material 125 to provide sufficient gain to overcome losses induced by, for example, coupling into and out of the build-up cavity 110. For example, the small-signal gain of the gain material 125 for the transmitted beam 122 can be greater than 10 dB (e.g., greater than 10 dB, greater than 10 dB, greater than 12 dB, greater than 15 dB, greater than 18 dB, greater than 20 dB, or greater than 25 dB, including any values and sub ranges in between).

The detector 130 in the system 100 is employed to detect the scattered light 118 and determine the presence or the absence of the substance of interest. In one example, the detector 130 can include a spectral detector (e.g., a grating in combination with a detector). In another example, the detector 130 includes a spectrometer to resolve different spectral components in the scattered light beam 118. The spectrometer can include a miniaturized spectrometer, such as a Talbot spectrometer, to achieve a desired form factor of the system 100. More information about miniaturized Talbot spectrometer can be found in PCT Application No. PCT/US2016/042512, which is hereby incorporated by reference in its entirety.

In yet another example, the detector 130 can include an intensity detector, such as a charge-coupled device (CCD) or a complementary metal-oxide-semiconductor (CMOS) detector. In this case, the system 100 can be used to detect the concentration level of known substance. A bandpass filter can be used before the detector 130 to transmit light at a specified wavelength (e.g., wavelength of a Raman peak) and block light at other wavelengths.

The system 100 can be used to detect various types of substances (i.e., the sample 101 can contain various types of substances of interest). For example, the substance of interest can include Tabun (also referred to as NA), Sarin (also referred to as GB), Soman (also referred to as GD), Isovanillin, Cyclosarin (also referred to as GF or cyclohexyl methylphosphonofluoridate), sulfur mustard (commonly known as mustard gas), $HN_3$, venomous Agent (also referred to as VX), hydrogen cyanide (also referred to as HCN, or AC), phosgene (also referred to as $COCl_2$ or CG), $H_2S$, $NH_3$, and $SO_2$, among others. In another example, the system 100 can be used to detect explosives. In yet another example, the system 100 can be used to detect biological agents such bacteria and/or virus (e.g., bacteria that can cause Anthrax).

The entire system 100 can also be integrated into a single device. For example, the system 100 can be configured into a hand-held device to allow convenient use in various conditions. In another example, the system 100 can be attached or integrated with an airplane or a drone for airborne operation. In yet another example, the system 100 can be attached to or integrated with a vehicle (e.g., a car, a robot, or any other vehicle). In these cases, the system 100 can operate in environments that may pose substantial danger to human beings.

The build-up cavity 110 includes two reflectors 112a and 112b to form a resonator to build up the intensity of the light beam 115 within the build-up cavity 110. In one example, the reflectors 112a and 112b can include dielectric mirrors, such as multilayer dielectric mirrors having high reflectivity at a specified wavelength. In another example, the reflectors 112a and 112b can include metallic mirrors or any other type of reflectors known in the art. In yet another example, the reflectors 112a and 112b can have a high-reflectivity coating on one side (e.g., the side toward the space between the two reflectors 112a and 112b) and an anti-reflection coating on the other side (e.g., the side opposite to the build-up cavity 110).

In general, high reflectivity of the reflectors 112a and 112b can increase the cavity finesse F and the intensity of the light beam 115. The finesse F can be calculated as $F \approx \pi \times$ Build-Up Factor$=\pi/(1-R)$, where R is the reflectivity of the reflectors 112a and 112b. (The Build-Up Factor represents the ratio of the circulating intensity inside of sample resonant cell to the incident intensity. In the case of a lossless, symmetrical cavity (i.e., where the mirror reflectivities are equal, R1=R2=R), the Build-Up Factor can be taken as $1/(1-R)$.) The finesse F is also related to the free spectral range (FSR) as F=FSR/FWHM, where FWHM is the full width at half maximum of a single transmission peak.

The finesse of the cavity 110 can be about 50 to about 500 (e.g., about 50, about 100, about 150, about 200, about 250, about 300, about 350, about 400, about 450, or about 500, including any values and sub ranges in between). Increasing the reflectivity can also decrease the spectral linewidth of the light beam 115. For example, the reflectivity of the reflectors 112a and 112b can be substantially equal to or greater than 95% (e.g., greater than 95%, greater than 96%, greater than 97%, greater than 98%, greater than 99%, greater than 99.2%, or greater than 99.5%, including any values and sub ranges in between).

The reflectivity of the reflectors 112a and 112b can also determine the quality factor of the build-up cavity 110. In practice, the quality factor of the build-up cavity can be substantially equal to or greater than 20 (e.g., greater than 20, greater than 30, greater than 50, greater than 100, greater than 150, greater than 200, greater than 300, greater than 500, or greater than 1000, including any values and sub ranges in between).

Due to the build-up of light intensity within the build-up cavity 110, the light beam 115 can be much more powerful than the transmitted beam 122 which oscillates within the main cavity 120. For example, the ratio of the intensity of the light beam 115 to the intensity of the transmitted beam 122 can be substantially equal to or greater than 100 (e.g., greater than 100, greater than 150, greater than 200, greater than 250, greater than 300, greater than 400, or greater than 500, including any values and sub ranges in between). The intensity of the transmitted beam 122 as used herein generally refers to the steady-state intensity of the light field within the main cavity 120.

The distance between the two reflectors 112a and 112b can be substantially equal to or less than 1 inch (e.g., less than 1 inch, less than 0.9 inch, less than 0.8 inch, less than 0.7 inch, less than 0.6 inch, less than 0.5 inch, less than 0.4 inch, or less than 0.3 inch, including any values and sub ranges in between). A shorter distance between the two reflectors 112a and 112b can decrease the total size of the system 100, thereby improving the portability of the system 100. On the other hand, however, a shorter distance between the two reflectors 112a and 112b may also increase the spectral linewidth of the light beam 115 oscillating within the build-up cavity. This decrease of spectral linewidth may be compensated for by increasing the reflectivity of the reflectors 112a and 112b.

As understood in the art, the build-up cavity 110 can define a series of equally-spaced cavity modes (i.e., peaks in spectrum; see, e.g., peaks 220 in FIG. 2 and description below). Each cavity mode has a spectral linewidth, and the distance between adjacent cavity modes (in terms of wavelength) is usually referred to as the free spectral range (FSR). In general, FSR can be calculated as FSR=c/2 nL, where c is the speed of light in vacuum, n is the refractive index inside the cavity, and L is the single pass length of the cavity.

Similarly, the main cavity 120 can also support a series of cavity modes (e.g., peaks 230 in FIG. 2 and description below), each of which has a linewidth determined by the length of the main cavity. Adjacent cavity modes are separated by a FSR. The light beam 115 that oscillates in the build-up cavity 110 is at a wavelength supported by one of the cavity modes of the build-up cavity 110. In addition, since part of the light beam 115 is also oscillating in the main cavity 120, the light beam 115 is one of the cavities modes of the main cavity 120. Therefore, it is desirable for at least one cavity mode of the build-up cavity 110 to overlap with at least one cavity mode of the main cavity 120. In this case, light beam at the wavelength of the overlapping cavity mode can oscillate in both cavities 110 and 120.

Figure 2:
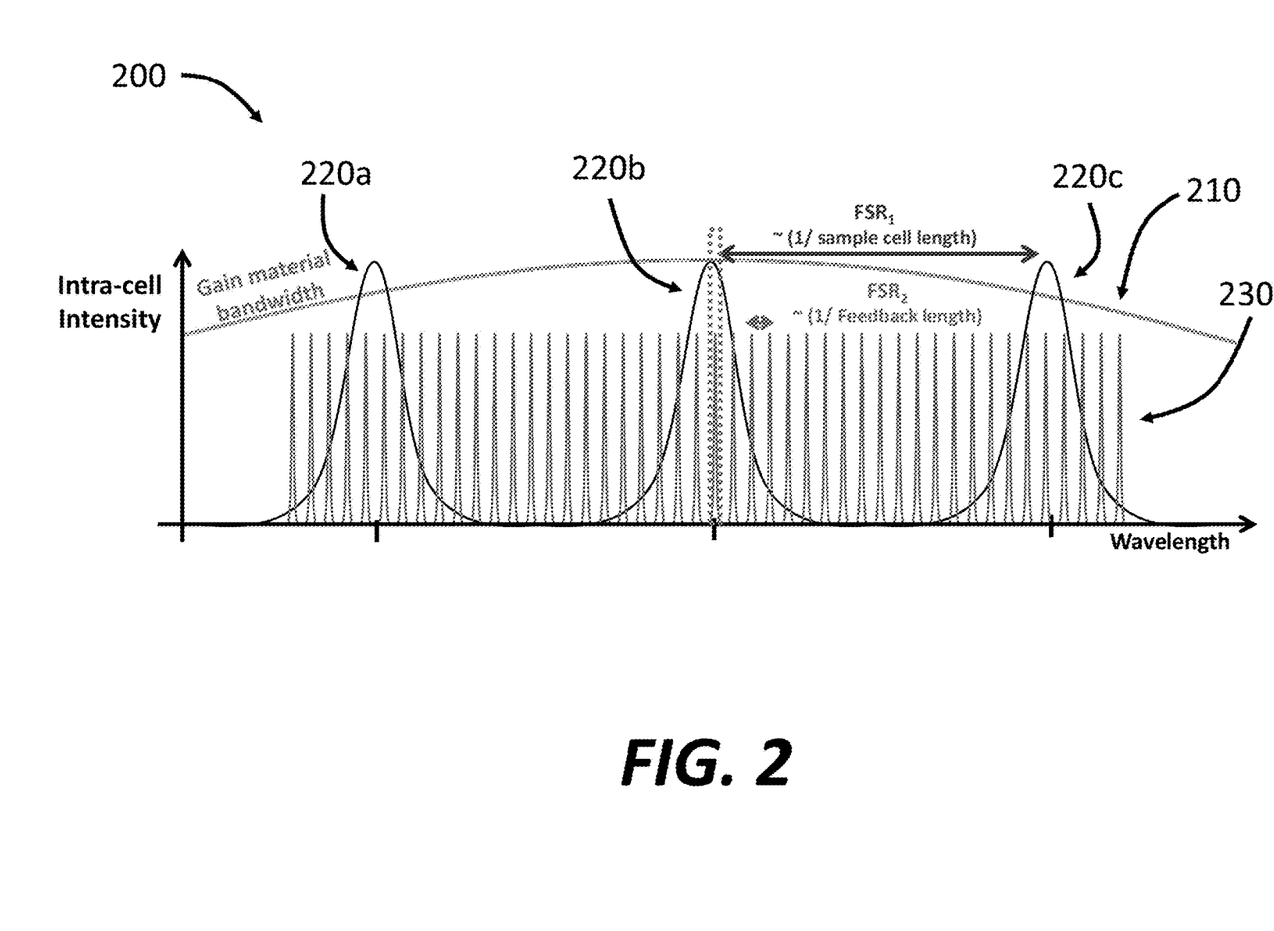
FIG. 2 shows the gain spectrum of the gain material, cavity modes of the main cavity, and cavity modes of the build-up cavity in the system shown in FIG. 1.

In practice, the spectral linewidth $\Delta v_b$ of the cavity modes of the build-up cavity 110 (e.g., indicated by peaks) can be greater than the FSR of the main cavity 120 (denoted as $FSR_m$, or $FSR_2$ in FIG. 2). As a result, at least one cavity mode of the main cavity 120 can be contained in the spectral peak of at least one cavity mode of the build-up cavity 110. The spectral linewidth $\Delta v_b$ can be defined as the full width at half maximum (FWHM) of the spectral peak. In one example, the ratio of $\Delta v_b$ over $FSR_1$ (i.e., $\Delta v_b/FSR_2$) can be substantially equal to or greater than one (e.g., greater than 1, greater than 1.5, greater than 2, greater than 3, greater than 4, greater than 5, greater than 10, greater than 20, greater than 30, greater than 40, or greater than 50, including any values and sub ranges in between).

The spectral linewidth $\Delta v_b$ of cavity modes in the build-up cavity 110 can also be larger than the spectral linewidth $\Delta v_m$ of cavity modes in the main cavity 120. In other words, the ratio of $\Delta v_b/\Delta v_m$ can be greater than 1 (e.g., greater than 1, greater than 2, greater than 5, greater than 10, greater than 15, or greater than 20, including any values and sub ranges in between).

The absolute value of the spectral linewidth $\Delta v_b$ of cavity modes in the build-up cavity 110 can also be the spectral linewidth of the light beam 115, which interacts with the sample 101 to generate a Raman signal indicating presence or absence of the substance of interest. The spectral linewidth of the light beam 115 can be no more than 60 GHz (e.g., about 60 GHz, about 50 GHz, about 40 GHz, about 30 GHz, about 20 GHz, about 10 GHz, about 5 GHz, about 2 GHz, about 1 GHz, about 500 MHz, about 300 MHz, or less, including any values and sub ranges in between).

As understood in the art, the distance $d_b$ between the two reflectors 112a and 112b can determine the optical path length $l_b$ of the build-up cavity 110 by $l_b=d_b/n_b$, where $n_b$ is the refractive index of the medium within the build-up cavity 110. Similarly, the main cavity 120 also has an optical path length $l_m$, which depends on the length of the main cavity 120 and the refractive index of medium in the main cavity 120. The optical path length $l_m$ can be substantially longer than the optical path length $l_b$ to achieve, for example, lasing at a desired wavelength. In practice, the ratio $l_m/l_b$ can be substantially equal to or greater than 100 (e.g., greater than 100, greater than 200, greater than 300, greater than 500, greater than 750, greater than 1000, greater than 2000, greater than 3000, greater than 4000, or greater than 5000, including any values and sub ranges in between).

The build-up cavity 110 can also improve the power stability of the light beam 115. This can allow the use of the intensity of the scattered light 118 as an indicator of the concentration of the substance of interest. The power variation (also referred to as power fluctuation) of the light beam 115 can be substantially equal to or less than 10% (e.g., less than 10%, less than 9%, less than 8%, less than 7%, less than 6%, or less than 5%, including any values and sub ranges in between). This power stability can be measured over an extended period of time greater than 1 hour (e.g., greater than 1 hour, greater than 5 hours, greater than 1 day or more, including any values and sub ranges in between).

FIG. 2 shows a plot 200 including an example of gain spectrum of the gain material 125, cavity modes of the main cavity 120, and cavity modes of the build-up cavity 110 in the system 100 shown in FIG. 1. The gain spectrum 210 has a large bandwidth, so only a portion of the gain spectrum 210 is shown in FIG. 2. The cavity modes 220a, 220b, and 220c (collectively referred to as 220) of the build-up cavity 110 have a narrower bandwidth $\Delta v_b$. The cavity modes 230 of the main cavity 120 have even narrower bandwidths $\Delta v_m$, compared to the bandwidth of the cavity modes 220.

As shown in FIG. 2, more than one cavity modes 230 can be contained within each cavity mode 220, in which case any light beam in those cavity modes 230 can oscillate in the system 100. In other words, the linewidth of the cavity modes 220 is greater than the FSR of the cavity modes 230 (i.e., the spacing between adjacent peaks of cavity modes 230).

Systems of Chemical Sensing Using Fiber Ring Resonators and Build-Up Cavities

Figure 3:
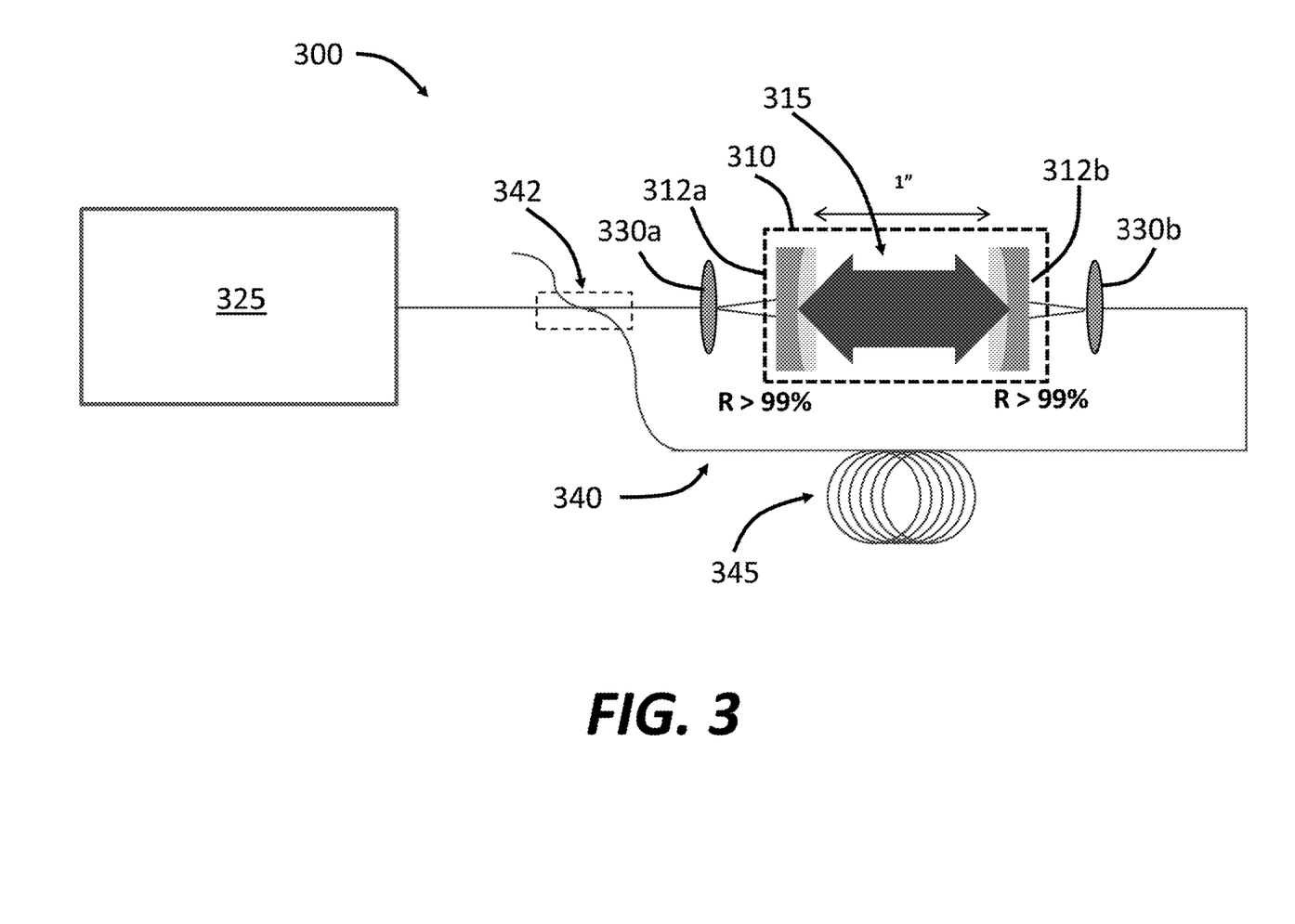
FIG. 3 shows a schematic of a chemical sensing system with a hybrid standing wave and fiber ring resonator with a build-up cavity within the fiber ring resonator.

FIG. 3 shows a schematic of a system 300 including a build-up cavity 310 disposed within a fiber ring resonator for substance sensing. The build-up cavity 310 includes a pair of reflectors 312a and 31b that define a space to receive a sample (not shown in FIG. 3). Each reflector 312a and 312b can have a reflectivity greater than 99%. A light beam 315 oscillates within the build-up cavity 310 and interacts with the sample to produce scattered light. The system 330 also includes a pair of lenses 330a and 330b disposed on two ends of the build-up cavity 310 to couple into (mode-match) only the fundamental mode of the build-up cavity. Coupling into other modes degrades the linewidth and decreases the build-up factor.

Part of the light beam 315 propagates through the build-up cavity 310. This transmitted beam propagates in a fiber ring resonator 340 for amplification. The fiber ring resonator 340 further includes a fiber loop 345, which can be a single-mode fiber, to set the desired FSR (also referred to as mode spacing) of cavity modes supported by the fiber ring resonator 340. The fiber ring resonator 340 also includes a coupler 342 to couple the transmitted beam into a gain material 325, which can be included in a fiber-coupled container. After amplification in the gain material 325, the light beam propagates back to the coupler 342, which then couples the amplified light beam to the build-up cavity 310.

In one example, the coupler 342 can include a fused fiber splitter. In another example, the coupler 342 can include a directional coupler. The directional coupler can be fabricated on or in a substrate and the fiber in the fiber ring resonator 340 can be end coupled to the directional coupler. In addition, the build-up cavity 310, the lenses 330a and 330b, and the gain material 325 can also be fabricated or disposed on the same substrate. Fibers can be used to connect together these components (i.e., the build-up cavity 310, the lenses 330a and 330b, and the gain material 325).

The optical path length of the fiber ring resonator 340 can be determined by the length of the fiber loop 345, which in turn can be conveniently adjusted. As understood in the art, changing the optical path length of the fiber ring resonator 340 can adjust the wavelength of cavity modes in the fiber ring resonator 340. In one example, the length of the fiber loop 345 can be adjusted to achieve a desired output wavelength and spectral linewidth of the light beam 315 before use of the system 300.

Figure 4:
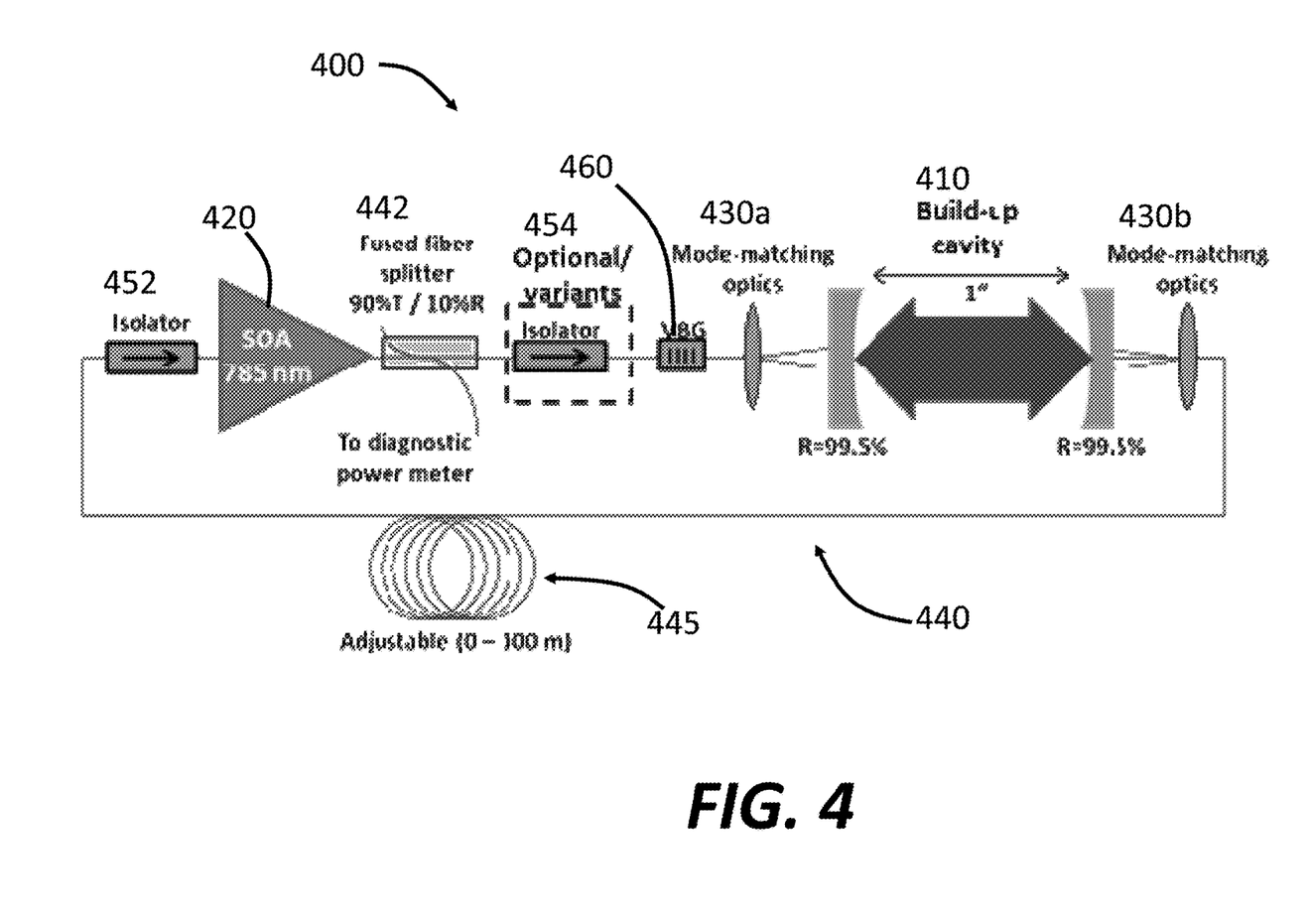
FIG. 4 shows a schematic of a chemical sensing system with a linear build-up cavity disposed within the fiber ring resonator.

FIG. 4 shows a schematic of a system 400 including a linear build-up cavity disposed within a fiber ring resonator. The system 400 includes a Semiconductor Optical Amplifier (SOA) 420 to amplify light beams propagating in the system 400. A fiber splitter 442 couples out a portion of the light beam for diagnostics (e.g., measuring the power). An optional isolator 454 can be optically coupled to the splitter 442 for protection optical components after the isolator 454. A volume Bragg grating (VBG) 460 is in optical communication with the optional isolator 454 to stabilize the wavelengths of light beams. After the VBG 460, the system 400 includes a build-in cavity 410 disposed between two mode-matching elements 430a and 430b. A fiber 445 then guides light beams after the build-in cavity 410 to an isolator 452 and back to the SOA 420, thereby forming a ring resonator 440.

The system 400 can operate at 785 nm with more than 1 watt of optical power inside the build-in cavity 410. The spectral linewidth of light beams in the build-in cavity 410 can be less than 50 GHz. The system 400 can operate with an electrical input less than 180 mW, thereby allowing convenient and portable operation in various conditions.

Methods of Chemical Sensing Using Build-Up Cavities

Figure 5:
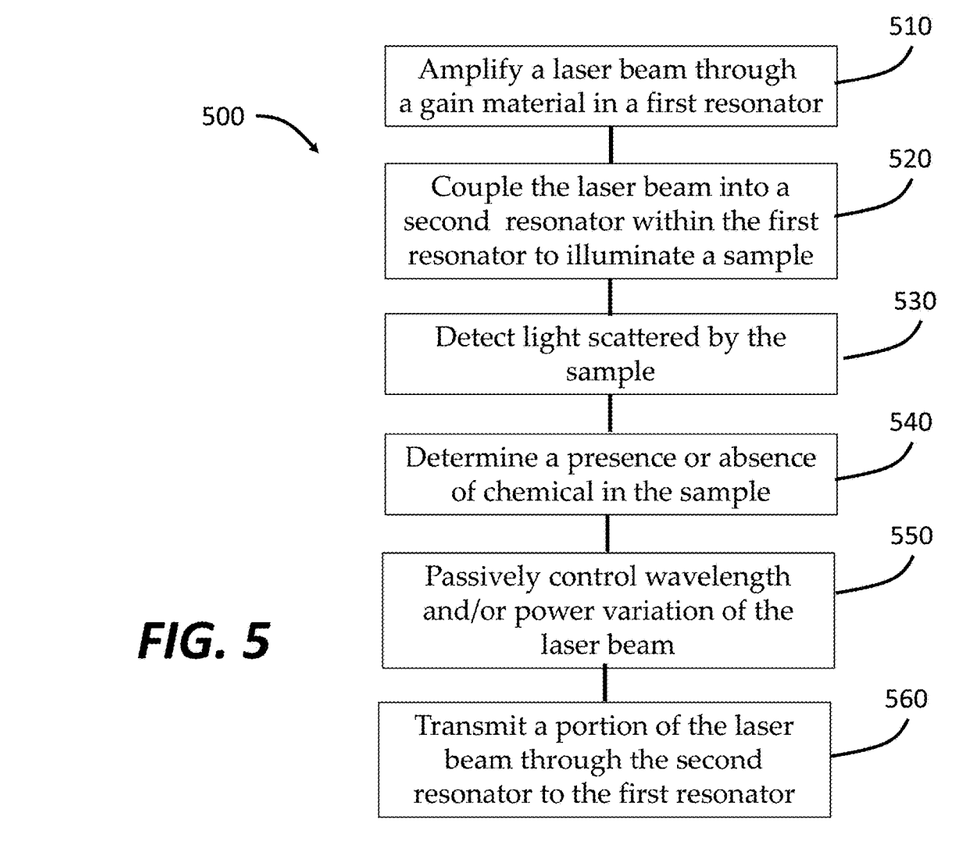
FIG. 5 illustrates a method for chemical sensing using a build-up cavity.

FIG. 5 illustrates a method 500 of chemical sensing using build-up cavities. At step 510 in the method 500, a laser beam is amplified through a gain material disposed in a first resonator to amplify the laser beam. Alternatively, the laser beam can be generated from spontaneous emission in the gain material and amplified by the same gain material. In one example, amplifying the laser beam includes transmitting the laser beam through a fiber ring resonator including the gain material. In another example, amplifying the laser beam includes transmitting the laser bean through a hybrid standing-wave and ring resonator. The gain material can include indium gallium nitride or aluminum gallium arsenide.

The laser beam is then coupled into a second resonator disposed within the first resonator at step 520. The second resonator receives a sample that may contain a substance of interest, such as chemicals or explosives. The laser beam oscillates in the second resonator to build up the intensity. The increased intensity of the laser beam can accordingly increase the strength of the interaction, such as Raman scattering, between the laser beam and the sample.

In one example, coupling the laser beam into the second resonator includes transmitting the laser beam into a linear cavity via a first reflector having a first reflectance greater than 95% and reflecting the laser beam off a second reflector disposed opposite the first reflector and having a second reflectance greater than 95%. The distance between the first reflector and the second reflector can be substantially equal to or less than one inch. At this step, illuminating the sample can include inducing Raman scattering or other scattering processes between the sample and the laser beam in the second resonator for chemical identification.

At step 530 in the method 500, a detector detects light scattered, reflected, or diffused by the interaction between the laser beam and the sample. The scattered light may have spectral components at wavelengths different from the wavelength of the laser beam. In one example, the detector can include a spectrometer to resolve different spectral components in the scattered light so as to determine a presence or absence of at least one chemical in the sample based at least in part on the light scattered by the sample, at step 540.

In another example, the wavelength of the scattered light may be determined beforehand. For example, the sample is known to contain a substance of interest and the method 500 can be used to estimate the concentration level of that substance of interest. In this case, the detector can just include an intensity detector.

The method 500 can also include step 550, at which the wavelength and/or the power variation of the laser beam is controlled. In one example, the linewidth of the laser beam can be controlled to be substantially equal to or less than 60 GHz. For substance sensing application, it can desirable to control the spectral linewidth of the laser beam. In one example, the second resonator (also referred to as a build-up resonator) within the first resonator can include two reflectors and the spectral linewidth can be increased by increasing the reflectivity of the two reflectors. In another example, the second resonator can include any other type of resonator known in the art and the spectral linewidth of the laser beam can be increased by increasing the quality factor of the second resonator.

The optical path length of the second resonator can also be increased or decreased to the linewidth of the laser beam. For example, the second resonator can be defined by two reflectors. At least one of the reflectors can be disposed on a translation stage so as to allow adjustment of the distance between the two reflectors so as to change the optical path length of the second resonator.

At step 550, the power variation of the laser beam can also be controlled to be less than 10%, which can be determined by the number of allowed modes the laser system can select from to operate and by the environmental disturbances. For example, the system can select from several modes to operate but the number of modes is not so many that different modes compete against each other and create power fluctuations.

The method 500 can further include a step 560 to transmit a portion of the laser beam through the second resonator to the first resonator. The transmitted portion of the laser beam can function as passive feedback to determine the frequency of the laser beam.

The method 500 can further include steps to change the optical path length of the first resonator so as to change the mode spacing and/or linewidth of modes in the first resonator. In one example, the first resonator can include a fiber ring resonator. In another example, the first resonator includes fiber in at least part of the beam path. In these cases, the optical beam path of the first resonator can be adjusted by changing the refractive index of the fiber in the first resonator. For example, the refractive index of the fiber can be changed by changing the temperature of the fiber (e.g., using a heater). In another example, mechanical forces can be used to change the refractive index of the fiber (e.g., by stretching the fiber). In yet another example, optical beams can be used to illuminate the fiber to change the refractive index of the fiber.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus for chemical sensing, the apparatus comprising:
    a first resonator;
    a gain material, disposed within the first resonator, to amplify a laser beam oscillating within the first resonator;
    a second resonator, disposed within the first resonator and in optical communication with the gain material, to receive a sample; and
    a detector, in optical communication with the sample, to detect light scattered by interaction between the sample and the laser beam.

2. The apparatus of claim 1, wherein the first resonator comprises a fiber ring resonator.

3. The apparatus of claim 1, wherein the gain material comprises indium gallium nitride.

4. The apparatus of claim 1, wherein the second resonator comprises:
    a first reflector having a first reflectance greater than 95%; and
    a second reflector disposed opposite the first reflector and having a second reflectance greater than 95%.

5. The apparatus of claim 4, wherein a distance between the first reflector and the second reflector is substantially equal to or less than one inch.

6. The apparatus of claim 1, wherein the second resonator has at least one resonant transmission peak having a linewidth with a full-width half-maximum that is greater than a free spectral range of the second resonator.

7. The apparatus of claim 1, wherein the first resonator has a first optical path length and the second resonator has a second optical path length, wherein the first optical path length is at least 100 times greater than the second optical path length.

8. The apparatus of claim 1, wherein the laser beam has a linewidth substantially equal to or less than 60 GHz.

9. The apparatus of claim 1, wherein the laser beam has a power variation less than 10%.

10. The apparatus of claim 1, wherein the second resonator has a quality factor greater than or equal to 20.

11. A method of chemical sensing, the method comprising:
    amplifying a laser beam with a gain material disposed in a first resonator;
    coupling the laser beam into a second resonator disposed within the first resonator; illuminating a sample disposed within the second resonator;
    detecting light scattered by the sample; and
    determining a presence or absence of at least one chemical in the sample based at least in part on the light scattered by the sample.

12. The method of claim 11, wherein amplifying the laser beam comprises transmitting the laser beam through at least one of a fiber ring resonator or a hybrid standing-wave and ring resonator.

13. The method of claim 11, wherein amplifying the laser beam comprises transmitting the laser beam through at least one of indium gallium nitride or aluminum gallium arsenide.

14. The method of claim 11, wherein coupling the laser beam into the second resonator comprises transmitting the laser beam into a linear cavity via a first reflector having a first reflectance greater than 95% and reflecting the laser beam off a second reflector disposed opposite the first reflector and having a second reflectance greater than 95%.

15. The method of claim 14, wherein a distance between the first reflector and the second reflector is substantially equal to or less than one inch.

16. The method of claim 11, further comprising:
    controlling a linewidth of the laser beam to be substantially equal to or less than 60 GHz.

17. The method of claim 11, further comprising:
    controlling a power variation of the laser beam to be less than 10%.

18. The method of claim 11, wherein coupling the laser beam into the second resonator comprises amplifying the laser beam by at least 20 times in the second resonator.

19. The method of claim 11, further comprising:
transmitting a portion of the laser beam through the second resonator to the first resonator.

20. The method of claim 11, wherein illuminating the sample comprises inducing Raman scattering between the sample and the laser beam in the second resonator for chemical identification.

21. A system for Raman sensing, the system comprising:
a ring resonator;
a gain material, disposed within the ring resonator, to amplify a laser beam propagating within the ring resonator;
a linear resonant cavity, disposed within the ring resonator and in optical communication with the gain material, to hold a sample that scatters a first portion of the laser beam and to transmit a second portion of the laser beam, the second portion of the laser beam providing passive feedback to stabilize a frequency of the laser beam; and
a detector, in optical communication with the sample, to detect the first portion of the laser beam.

* * * * *